(12) United States Patent
Xu et al.

(10) Patent No.: US 9,506,003 B2
(45) Date of Patent: Nov. 29, 2016

(54) LUBRICANTS FOR MAGNETIC RECORDING MEDIA

(71) Applicant: Agency for Science, Technology and Research, Singapore (SG)

(72) Inventors: Jianwei Xu, Singapore (SG); Rong Ji, Singapore (SG); Xiaobai Wang, Singapore (SG); Ching Mui Cho, Singapore (SG); Yan Xuan Angeline Tan, Singapore (SG); Chaobin He, Singapore (SG); Huiqing Xie, Singapore (SG); Wen Huei Jack Tsai, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 116 days.

(21) Appl. No.: 14/419,771

(22) PCT Filed: Aug. 7, 2013

(86) PCT No.: PCT/SG2013/000336
§ 371 (c)(1),
(2) Date: Feb. 5, 2015

(87) PCT Pub. No.: WO2014/025316
PCT Pub. Date: Feb. 13, 2014

(65) Prior Publication Data
US 2015/0218480 A1    Aug. 6, 2015

(30) Foreign Application Priority Data
Aug. 8, 2012   (SG) ............... 201205891-3

(51) Int. Cl.
*C10M 105/74*   (2006.01)
*C08K 5/5399*   (2006.01)
(Continued)

(52) U.S. Cl.
CPC ............ *C10M 105/74* (2013.01); *C07F 9/659* (2013.01); *C07F 9/65815* (2013.01);
(Continued)

(58) Field of Classification Search
CPC ............ C10M 105/74; C10M 107/48; C10M 2223/083; C10M 2225/0405; C10N 2220/022; C10N 2220/14; C10N 2230/02; C10N 2230/08; C10N 2240/204; C10N 2270/00; C08K 5/5399; C07F 9/65815; C07F 9/659
USPC ................................................. 508/548, 422
See application file for complete search history.

(56) References Cited

U.S. PATENT DOCUMENTS 6,482,910 B1 * 11/2002 Allcock ................ C08F 132/08
   526/233
7,579,304 B2 * 8/2009 Liu ........................ G11B 5/725
   508/422
(Continued)

FOREIGN PATENT DOCUMENTS

WO   2008008041 A1   1/2008

OTHER PUBLICATIONS

Written Opinion of the International Searching Authority for International Application No. PCT/SG2013/000336 dated Sep. 27, 2013, pp. 1-5.
(Continued)

*Primary Examiner* — James Goloboy
(74) *Attorney, Agent, or Firm* — Winstead, P.C.

(57) ABSTRACT

The invention relates to lubricants for magnetic recording media, and in particular, to such lubricants containing cyclotriphosphazene. Methods for preparing the lubricants are also disclosed.

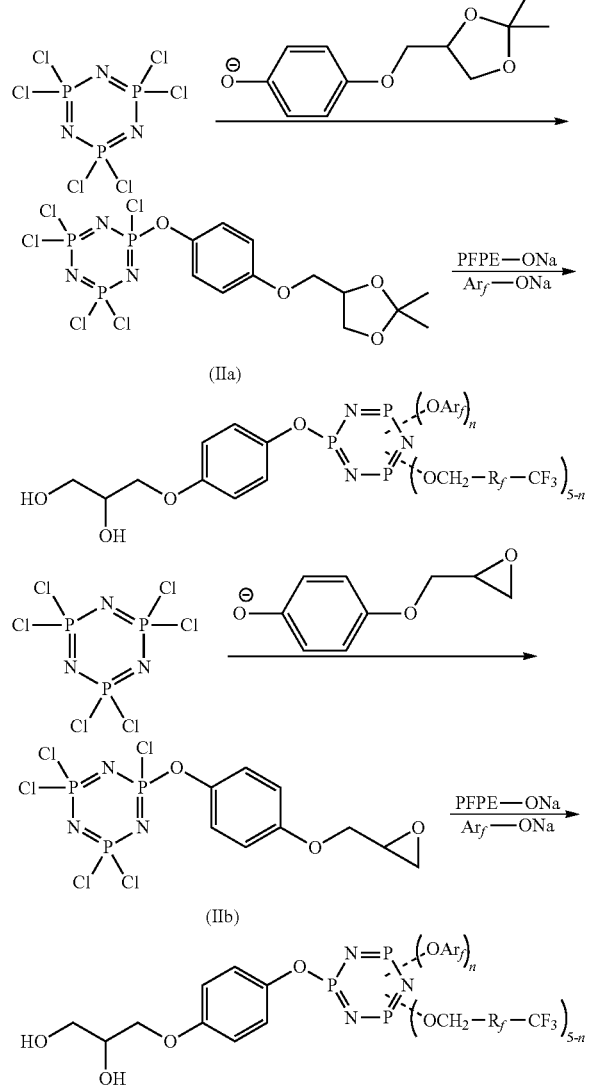

12 Claims, 4 Drawing Sheets (51) Int. Cl.
*C07F 9/6581* (2006.01)
*C07F 9/6593* (2006.01)
*C07F 9/659* (2006.01)
*C10M 107/48* (2006.01)

(52) U.S. Cl.
CPC ......... *C10M 107/48* (2013.01); *C08K 5/5399* (2013.01); *C10M 2223/083* (2013.01); *C10M 2225/0405* (2013.01); *C10N 2220/022* (2013.01); *C10N 2220/14* (2013.01); *C10N 2230/02* (2013.01); *C10N 2230/08* (2013.01); *C10N 2240/204* (2013.01); *C10N 2270/00* (2013.01)

(56) References Cited

U.S. PATENT DOCUMENTS

| | | | |
|---|---|---|---|
| 7,772,172 B2* | 8/2010 | Liu | G11B 5/725 427/558 |
| 7,833,641 B2 | 11/2010 | Tomiyasu et al. | |
| 7,968,505 B2 | 6/2011 | Liu et al. | |
| 8,063,003 B2 | 11/2011 | Di Meo et al. | |
| 2009/0297887 A1 | 12/2009 | Liu et al. | |
| 2011/0064970 A1* | 3/2011 | Chen | C10M 157/10 428/800 |
| 2011/0143165 A1 | 6/2011 | Kobayashi et al. | |

OTHER PUBLICATIONS

International Preliminary Report on Patentability for International Application No. PCT/SG2013/000336 dated Feb. 19, 2015, pp. 1-7.

\* cited by examiner

LUBRICANTS FOR MAGNETIC RECORDING MEDIA

CROSS-REFERENCE TO RELATED APPLICATION

This application claims the benefit of priority of Singapore Patent Application No. 201205891-3, filed Aug. 8, 2012, the contents of which being hereby incorporated by reference in its entirety for all purposes.

TECHNICAL FIELD

The invention relates to lubricants for magnetic recording media, and in particular, to such lubricants containing cyclotriphosphazene.

BACKGROUND

Due to the continuous increase in magnetic recording densities, small distance head-disk, and increase in the rotation speed of the disk, conventional lubricants are facing several obstacles, such as weak durability, heavy lubricant pickup, and uncontrollable friction. The media surface must be well protected from damage due to sporadic contacts with the disk head when it flies over the disk. Therefore, hard disk media with good wear durability is very important to ensure the reliability of a hard disk drive and to prevent the disk from damage caused by poor performance of the lubricant.

Typically, a very thin lubricant film with 1-2 nm thickness is deposited onto a hard disk surface and the lubricant film ought to provide sufficient protection to the hard disk surface. When the disk head flies over an area of the disk surface, a portion of the lubricant film is replaced and lubricant in close proximity flows back to the lubricant-depleted area in a certain time period to cover the zone that the lubricant coverage is depleted before the disk head flies over the same area again. It thus requires lubricant to have sufficient mobility which is capable of repairing the damaged area within an allowable time period in order to prevent disk failure.

Lubricants with poor mobility need a longer time to flow into the lubricant-depleted area. As a result, there is a possibility that the disk head flies back to the lubricant-depleted area which is not sufficiently covered up by the adjacent lubricant, thus resulting in disk failure. In contrast, high mobility leads to fast replenishment of the lubricants. In theory, lubricants with sufficiently high surface mobility are able to effectively prevent damage of the disk. Enhancement of lubricant surface mobility may be achieved by designing a lubricant with either a relatively low molecular weight or with terminal groups that have weak interaction with the disk surface.

In any case, both alternatives pose problems. For example, on one hand, a lubricant with a low molecular weight usually has relatively high volatility and subsequently results in fast evaporative loss during a long term usage. On the other hand, the weak interaction between the lubricant and the hard disk surface makes it difficult for the lubricant to bond to the hard surface, leading to poor bonding of lubricant to the disk surface and inevitably causing disk damage.

Therefore, there remains a need to provide lubricants that overcomes, or at least alleviates, the above problems.

SUMMARY

Present invention relates to the synthesis of cyclotriphosphazene containing lubricants including at least one of a perfluoropolyether (PFPE) group, a fluorinated aryloxy group and an aryloxy group substituted with a hydrophilic group. The hydrophilic group may be 2,3-dihydroxypropoxy. The hydrophilic group may be substituted at para, or meta, or ortho position of the aryloxy group.

Thus, in a first aspect of the disclosure, there is provided a compound of formula (I)

wherein n in formula (I) is 0, 1, 2, 3, or 4;

m in formula (I) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F;

each $OAr_f$ is a different or a same fluorinated C6-C20 aryloxy group; and $R_f$ is selected from the group consisting of $CF_2CF_2O(CF_2CF_2CF_2O)_rCF_2CF_2$ wherein r is 2 to 30 and $CF_2(OCF_2CF_2)_sO(CF_2)_t$ wherein s is 2 to 30 and t is 0, 1, 2, or 3.

In a second aspect of the disclosure, there is provided an intermediate compound of formula (IIa) or (IIb)

wherein n in formula (IIa) or (IIb) is 4 or 5;

m in formula (IIa) or (IIb) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F.

In a third aspect of the disclosure, a method for forming the intermediate compound of the second aspect is disclosed. The method may include:

reacting hexachlorocyclotriphosphazene with a phenoxide of formula (IIIa) or (IIIb)

in a tetrahydrofuran solvent to form the intermediate compound of formula (IIa) or (IIb), respectively.

In a fourth aspect of the disclosure, there is disclosed a method for forming the compound of formula (I). The method may include:
reacting the intermediate compound of formula (IIa) or (IIb) with NaOAr$_f$ and NaOCH$_2$—R$_f$—CF$_3$ in a tetrahydrofuran solvent,
wherein
OAr$_f$ is a fluorinated C6-C20 aryloxy group; and
R$_f$ is selected from the group consisting of CF$_2$CF$_2$O (CF$_2$CF$_2$CF$_2$O)$_r$CF$_2$CF$_2$ wherein r is 2 to 30 and CF$_2$(OCF$_2$CF$_2$)$_s$O(CF$_2$)$_t$ wherein s is 2 to 30 and t is 0, 1, 2, or 3.

In a fifth aspect of the disclosure, use of the compound of formula (I) as a lubricant is disclosed.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural changes may be made without departing from the scope of the invention. The various embodiments are not necessarily mutually exclusive, as some embodiments can be combined with one or more other embodiments to form new embodiments.

Currently, there are some commercial lubricants which have high bonding ratio, such as A20H and Z-tetraol. However, disk failure caused by lubricants, such as heavy pickup of the lubricants during the operation, is still a problem.

To this end, present inventors have found that by linking cyclotriphosphazene with aromatic groups and perfluoropolyether (PFPE), particularly an aryloxy group substituted with a hydrophilic moiety, the interaction between a lubricant and a magnetic recording medium surface is enhanced. Such lubricants are able to provide for a balanced retention and replenishment properties. For example, in addition to introducing cyclotriphosphazene into a lubricant molecule, a hydrophilic moiety with two hydroxy groups is also introduced which can act as anchoring points for the lubricant molecule to adhere tightly onto the carbon overcoat surface of a magnetic record medium, thus significantly enhancing the interaction of lubricant and magnetic recording medium surface. In the examples given in later paragraphs, present lubricant IDL4 shows comparable surface mobility to A20H and higher mobility than Z-tetraol. However, present lubricant IDL4 shows significant improvement in the bonding ratio (without treatment), and its bonding ratio is higher than some market lubricants such as A20H, Zdol, and Z-tetraol. This can help solve the pickup problem of the lubricant in some cases.

Specifically, lubricants including at least one of a perfluoropolyether (PFPE) group, a fluorinated aryloxy group and an aryloxy group substituted with a hydrophilic group are preferred. The hydrophilic group may be 2,3-dihydroxypropoxy. The hydrophilic group may be substituted at para, or meta, or ortho position of the aryloxy group.

Accordingly, in a first aspect of the disclosure, there is provided a compound of formula (I)

wherein
n in formula (I) is 0, 1, 2, 3, or 4;
m in formula (I) is 0, 1, 2, 3, or 4;
each R', when present, is a different or a same substituent selected from the group consisting of C1-C10 alkyl, C1-C10 alkoxy, C1-C10 perfluorinated alkyl, C1-C10 perfluorinated alkoxy, and F;
each OAr$_f$ is a different or a same fluorinated C6-C20 aryloxy group; and
R$_f$ is selected from the group consisting of CF$_2$CF$_2$O (CF$_2$CF$_2$CF$_2$O)$_r$CF$_2$CF$_2$ wherein r is 2 to 30 and CF$_2$(OCF$_2$CF$_2$)$_s$O(CF$_2$)$_t$ wherein s is 2 to 30 and t is 0, 1, 2, or 3.

The term "perfluorinated" means an organic compound including all hydrogens replaced by fluorine on a carbon chain but the compound also contains at least one different atom or functional group.

The term "alkyl", alone or in combination, refers to a fully saturated aliphatic hydrocarbon. In certain embodiments, alkyls are optionally substituted. In certain embodiments, an alkyl comprises 1 to 10 carbon atoms, for example 1 to 6 carbon atoms, wherein (whenever it appears herein in any of the definitions given below) a numerical range, such as "1 to 10" or "C1-C10", refers to each integer in the given range, e.g. "C1-C10 alkyl" means that an alkyl group comprising 1, 2, 3, 4, 5, 6, 7, 8, 9, or 10 carbon atoms. Examples of alkyl groups include, but are not limited to, methyl, ethyl, n-propyl, isopropyl, n-butyl, isobutyl, sec-butyl, tert-butyl, pentyl, hexyl, heptyl, octyl and the like.

The term "alkoxy", alone or in combination, refers to an aliphatic hydrocarbon having an alkyl-O— moiety. In certain embodiments, alkoxy groups are optionally substituted. In certain embodiments, an alkoxy comprises 1 to 10 carbon atoms ("C1-C10 alkoxy"), i.e. including 1, 2, 3, 4, 5, 6, 7, 8, 9, or 10 carbon atoms. Examples of alkoxy groups include, but are not limited to, methoxy, ethoxy, propoxy, butoxy and the like.

The term "aryloxy", alone or in combination, refers to both an —O-aryl and an —O-heteroaryl group. In certain embodiments, aryloxy groups are optionally substituted. In certain embodiments, an aryloxy comprises 6 to 20 carbon atoms, ("C6-C20 aryloxy"), i.e. including 6, 7, 8, 9, 10, 11, 12, 13, 14, 15, 16, 17, 18, 19, or 20 carbon atoms. Examples include and are not limited to phenoxy, napthyloxy, pyridyloxy, furanyloxy, and the like.

In various embodiments, n is 1, 2, 3, or 4.

In certain embodiments, each R', when present, is F.

In formula (I), $R_f$ can be $CF_2CF_2O(CF_2CF_2CF_2O)_rCF_2CF_2$ and r is 2 to 30, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In various embodiments, $R_f$ is $CF_2CF_2O(CF_2CF_2CF_2O)_rCF_2CF_2$ where r is 21.

Alternatively, in formula (I), $R_f$ can be $CF_2(OCF_2CF_2)_sO(CF_2)_t$ and s is 2 to 30, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30, and t is 0, 1, 2, or 3.

In various embodiments, $R_f$ is $CF_2(OCF_2CF_2)_sO(CF_2)_t$ where s is 2 and t is 3.

In various embodiments, m in formula (I) is 0.

In yet further embodiments, m in formula (I) is 0 and the hydrophilic group 2,3-dihydroxypropoxy is substituted at para position of the aryloxy group, as shown below:

In various embodiments, $OAr_f$ is a fluorinated phenoxy group selected from the group consisting of 4-(trifluoromethyl)phenoxy (i.e. p-$CF_3C_6H_4O$), 4-fluorophenoxy (i.e. p-F—$C_6H_4O$), and pentafluorophenoxy (i.e. $C_6F_5O$).

It has been found by the inventors that compounds of formula (I) can be used as lubricants, and in particular, for lubricating magnetic recording medium. For example, lubricants containing compounds of formula (I) can have a high bonding ratio without treatment, moderate mobility, and relatively higher thermal stability.

In a second aspect of the disclosure, there is provided an intermediate compound of formula (IIa) or (IIb)

wherein n in formula (IIa) or (IIb) is 4 or 5;

m in formula (IIa) or (IIb)) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F.

Based on the above, two key intermediate compounds of formulae (IIa) and (IIb) for the preparation of lubricants of compounds of formula (I) are also disclosed.

To form the respective intermediate compounds of formulae (IIa) and (IIb), hexachlorocyclotriphosphazene is reacted with a phenoxide of formula (IIa) or (IIIb)

in a tetrahydrofuran solvent to form the intermediate compound of formula (IIa) or (IIb), respectively.

In one specific embodiment, the intermediate compound of formula (IIa), i.e. 4-(2,3-dihydroxypropoxy)aryloxy-pentachlorocyclotriphosphazene, is prepared by mixing hexachlorocyclotriphosphazene with sodium 4-((2,2-dimethyl-1,3-dioxolan-4-yl)methoxy)phenolate in an organic solvent such as tetrahydrofuran (THF). Sodium 4-((2,2-dimethyl-1,3-dioxolan-4-yl)methoxy)phenolate may be prepared by a reaction between 4-((2,2-dimethyl-1,3-dioxolan-4-yl)methoxy)phenol and a base solution including $K_2CO_3$, $Na_2CO_3$, KOH, NaOH or NaH in an organic solvent such as THF. Other than THF, other organic solvents such as benzene, methylbenzene, or the like are also useful.

For example, the intermediate compound of formula (IIa) may be prepared as follows: To a dry THF solution of 4-((2,2-dimethyl-1,3-dioxolan-4-yl)methoxy)phenol (0.05 mol), sodium hydride (0.06 mol) was added. The reaction was stirred at 60° C. for 2 h and hexachlorocyclotriphosphazene was added in one portion. The mixture was stirred for 12 h. The product was separated by silica gel column chromatography. The structure and purity of pentachloro-6-[4-(2,2-dimethyl-1,3-dioxolan-4-yl)methylphenoxy]-cyclotriphosphazene was confirmed by $^1$H and $^{31}$P NMR.

After forming the intermediate compound of formula (IIa) or (IIb), the respective intermediate compound of formula (IIa) or (IIb) is reacted with NaOAr$_f$ and NaOCH$_2$—R$_f$—CF$_3$ in a tetrahydrofuran solvent,
wherein
OAr$_f$ is a fluorinated C6-C20 aryloxy group; and
R$_f$ is selected from the group consisting of CF$_2$CF$_2$O(CF$_2$CF$_2$CF$_2$O)$_r$CF$_2$CF$_2$ wherein r is 2 to 30 and CF$_2$(OCF$_2$CF$_2$)$_s$O(CF$_2$)$_t$ wherein s is 2 to 30 and t is 0, 1, 2, or 3.

Figure 1:
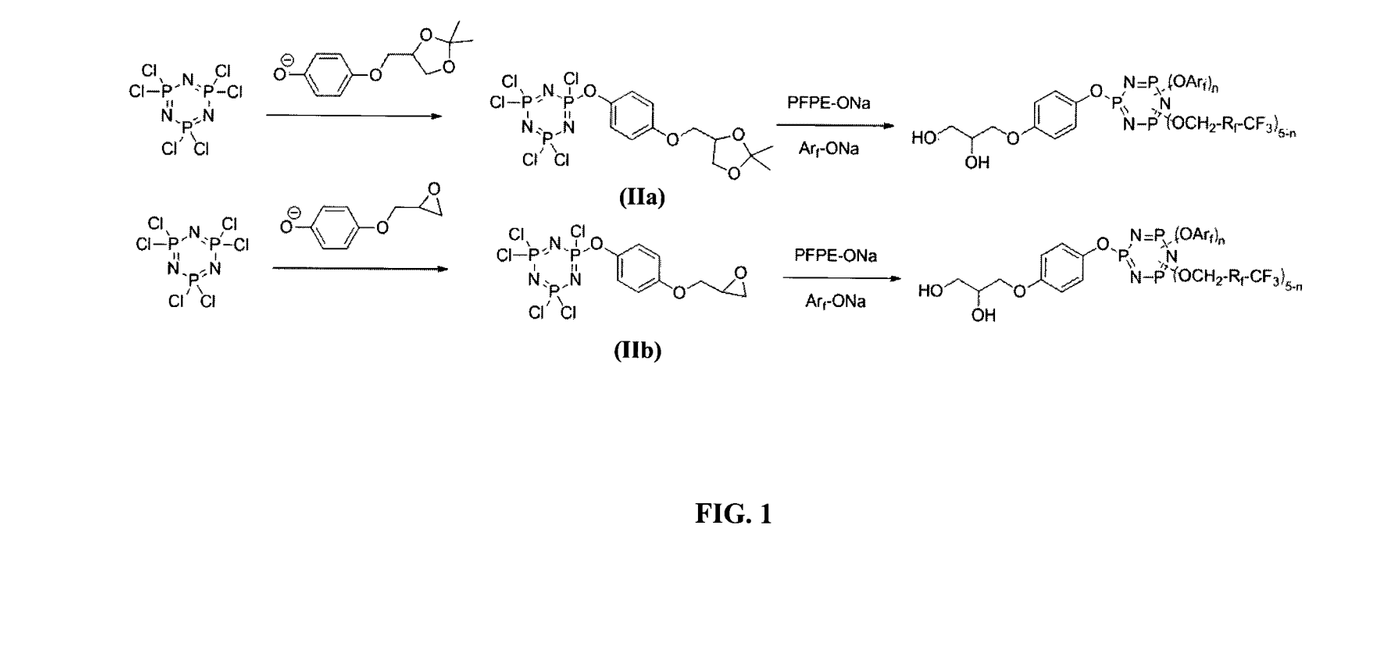
FIG. 1 shows a scheme of a chemical reaction process of forming exemplary embodiments of compounds of formula (I).
Figure 2:
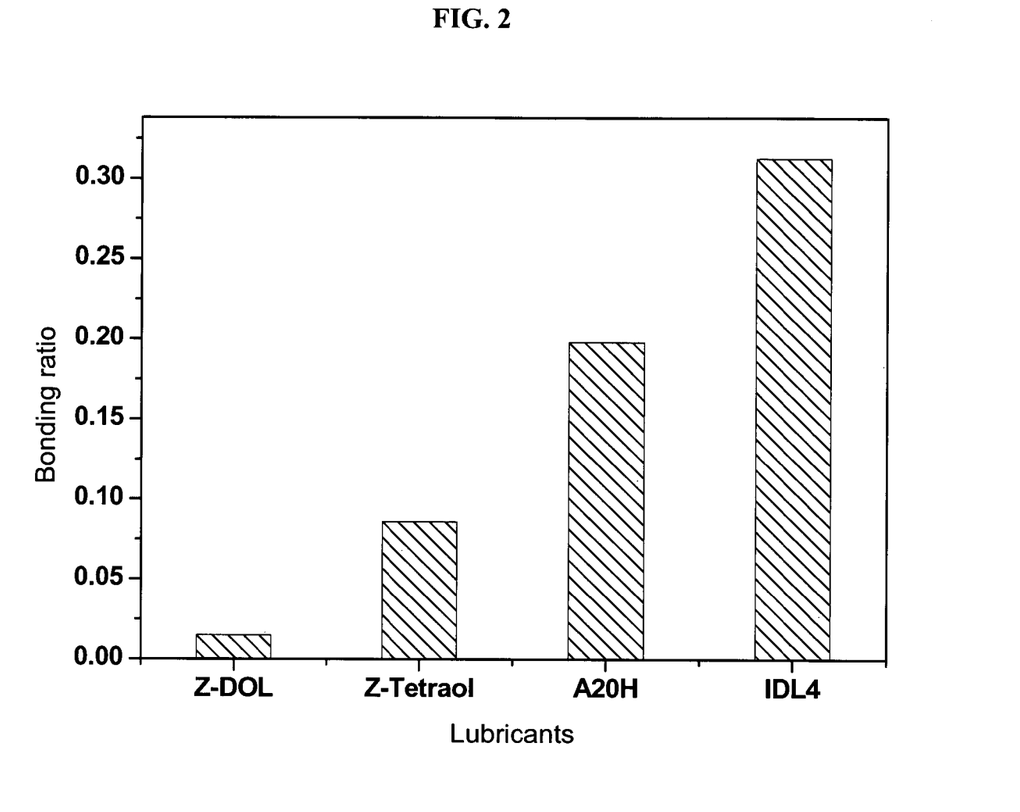
FIG. 2 shows a bar graph of lubricant bonding ratio (without any treatment) for various lubricants.

The method for forming the compound of formula (I) is shown in FIG. 1.

The reaction may be carried out in the presence of a base such as NaH, NaOH, KOH, Na$_2$CO$_3$, Cs$_2$CO$_3$, and the like.

In various embodiments, OAr$_f$ is a fluorinated C6-C20 aryloxy group such as a fluorinated phenoxy group selected from the group consisting of 4-(trifluoromethyl)phenoxy (i.e. p-CF$_3$C$_6$H$_4$O), 4-fluorophenoxy (i.e. p-F—C$_6$H$_4$O), and pentafluorophenoxy (i.e. C$_6$F$_5$O).

In various embodiments, NaOCH$_2$—R$_f$—CF$_3$ is formed from a hydroxy-terminated PFPE in a mixture of organic and perfluorinated solvents in the presence of sodium hydride at a temperature range of 50-250° C.

In certain embodiments, R$_f$ is CF$_2$(OCF$_2$CF$_2$)$_3$O(CF$_2$)$_3$ or CF$_2$(OCF$_2$CF$_2$)$_3$OCF$_2$CF$_2$.

In summary, presently disclosed compounds and lubricants exhibit moderate mobility which is most desirable for hard disk drive industry applications. It shows higher bonding ratio than conventional lubricants that have been using for many years by hard disk drive industry. Furthermore, it exhibits similar tribological performance to the commercial lubricants.

Present lubricants can be used as lubricants or additives alone, or in combination with the commercial products to achieve better performance such as high thermal stability, and optimized mobility.

In order that the invention may be readily understood and put into practical effect, particular embodiments will now be described by way of the following non-limiting examples.

EXAMPLES

Example 1

Preparation of IDL4

Perfluoropolyether and perfluorinated aromatic phenol in 100 ml dry THF was added dropwise into a suspension of sodium hydride in 150 ml THF. The reaction was heated at 40° C. for 24 h with N$_2$ gas protection. Pentachloro-[4-(2,2-dimethyl-1,3-dioxolan-4-yl)methylphenoxy]-cyclotriphosphazene dissolved in dry THF was then added, the temperature was raised to 70° C. and the reaction mixture was maintained at this temperature for 48 h. After the reaction was completed, THF was removed, and the oily milky mixture was washed with water 3 times (250 ml×3). The resulting clear oil was dried under vacuum for 12 h.

Then, 20 ml of H$_2$SO$_4$ solution (0.1 M) was added into the above clear oil, and the mixture was stirred at 40° C. for a few hours. Once the reaction has completed, the reaction mixture was washed with water (100 ml×3) to remove the acid. Finally, the product was dried in vacuum at 80° C. overnight. NMR (400 MHz, CDCl$_3$): δ 3.65-4.50 (m, br., 15H); 6.8 (m, br., 2H); 7.04 (m, br., 2H). $^{31}$P NMR (CDCl$_3$): δ=17.4 (s, br).

Example 2

Viscosity Measurement

Similar to commercial hard disk lubricants, the viscosity of IDL4 has shown to behave like a Newtonian liquid. The dynamic viscosity data of lubricant IDL4 and some commercial available lubricants at 25° C. are summarized in Table 1.

TABLE 1

Viscosity Data for Selected Lubricants vs. Commercial Products.

| Lubricant | Viscosity at 25° C. (mPa · s) |
| --- | --- |
| IDL4 | 30 |
| Z-DOL(2K) | 28 |
| Z-DOL(4K) | 77 |
| X1-p | 729 |
| A20H | 65 |
| Z-tetraol | 500 |

Example 3

Bonding Ratio Measurement

Media lubricant bonding ratio is defined as the ratio of bonded lubricant thickness to total lubricant thickness of the lubricant film. The narrow scan signal of C1s was obtained on a PHI Quantera SXM Scanning X-ray Microprobe. The lubricant film thickness was calculated based on the ratio of the C1s peak from the lubricant (C—F) and the substrate (C—C/C—H) after the correction of the overlap of the C—C/C—H peaks from the lubricant. The lubricated film thickness was controlled by adjusting the dipping in and withdrawing out speed after calibration by XPS. The bonded lubricant film is obtained after washing away the mobile lubricant. The bonding ratio given in Table 2 shows that the new product IDL4 has very high bonding ratio measured under the same experimental conditions.

TABLE 2

| Bonding ratio* | |
| --- | --- |
| Lubricant | Bonding ratio % |
| IDL4 | 31.3 |
| Z-DOL(2K) | 1.5 |
| A20H(3K) | 19.8 |
| Z-tetraol | 8.6 |

*Without post-treatment

Example 4

Water Contact Angle Measurement of Lubricant Thin Films

The water contact angles of the lubricants were measured using a RameHart™ contact angle goniometer. Under the same measurement conditions, the water contact angle of IDL4 was found to be comparable with commercial lubricant as shown in Table 3.

TABLE 3

Water Contact Angle Comparison

| Lubricant | Contact Angle (°) @ 25° C. |
|---|---|
| IDL4 | 80 |
| Z-DOL(2.5K) | 78 |
| A20H(3K) | 82 |
| Z-tetraol | 85 |

Example 5

Lubricant Mobility Measurement

Figure 3:
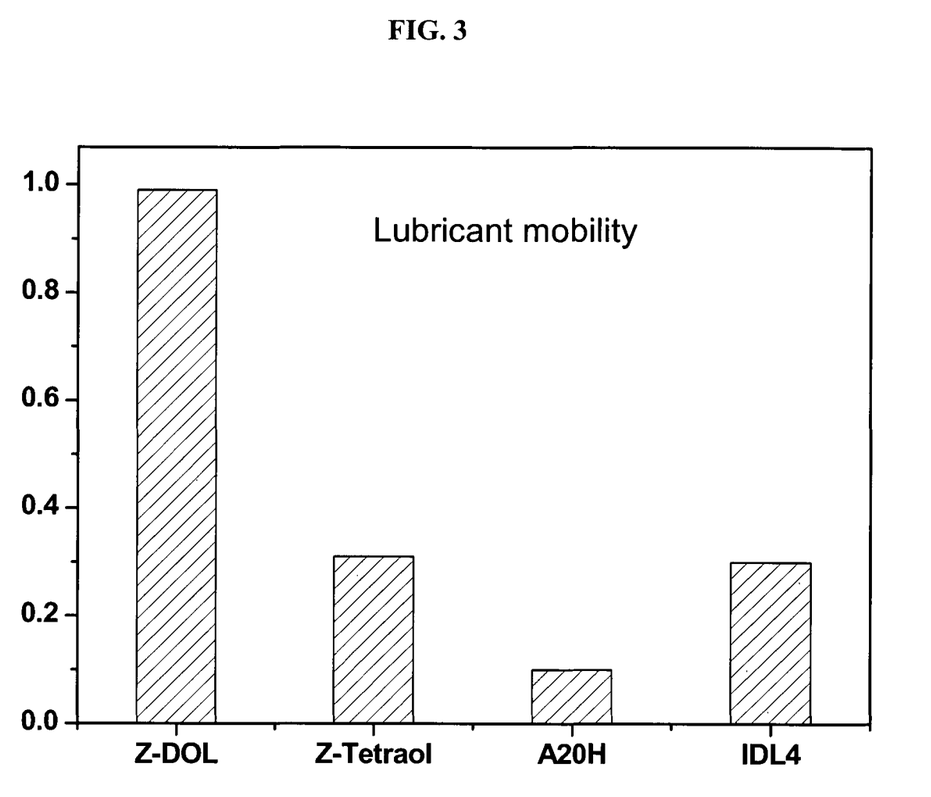
FIG. 3 shows a bar graph of lubricant mobility for various lubricants.

The mobility of the lubricants was tested using TOF-SIMS. In the test, a film of each respective lubricant was formed uniformly on a disk surface. A local area in the film (a radial "stripe" approximately 40 µm wide) was depleted of the lubricant. The rate at which each lubricant film flew back into the depleted area on the disk surface was measured using TOF-SIMS. The recovery by the respective lubricant in the depleted area after 1 h was examined, and the recovery rate was used to indicate the lubricant film mobility. As shown in FIG. 3, the mobility of A20H film was found to be much lower than that of Zdol 2000 film. In contrast, lubricant IDL4 showed a moderate mobility. As can be appreciated, excess mobility may lead to lubricant spin-off and lubricant film dewetting, decreasing the durability of the hard disk; while poor mobility may result in loss of lubrication in some areas on the disk surface. Thus, a moderate mobility may be desirable for a lubricant used in magnetic recording applications.

Example 6

Lubricant Friction Measurement

Figure 4:
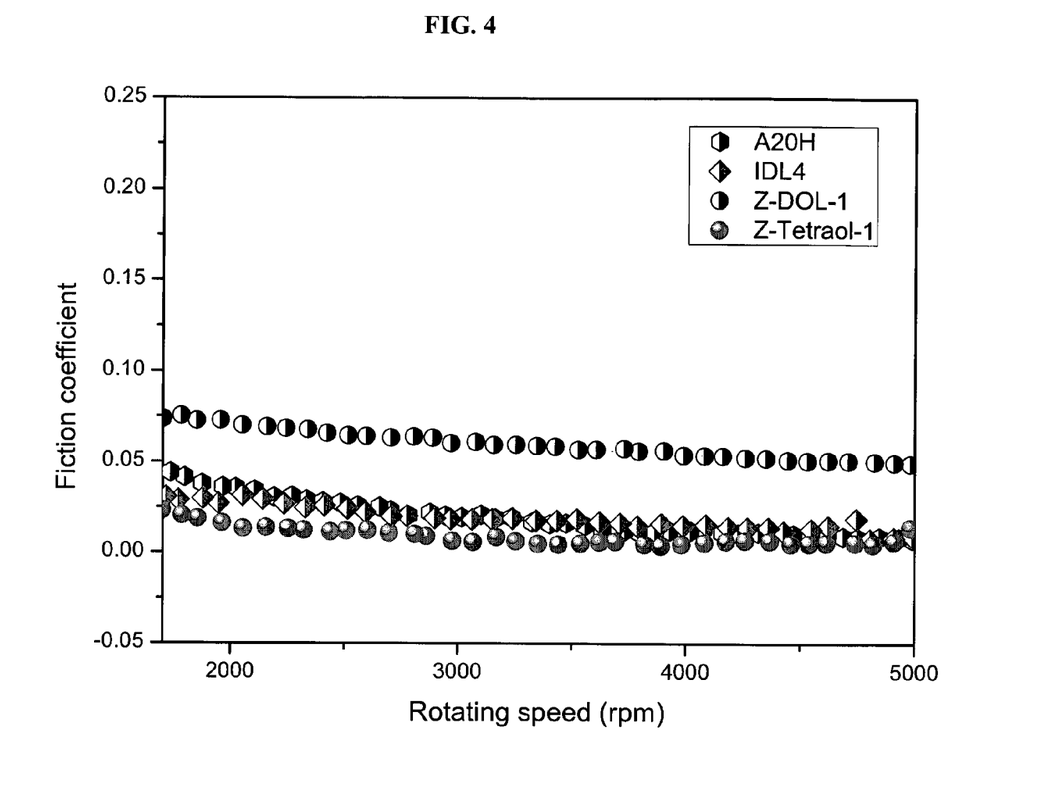
FIG. 4 shows a bar graph of lubricant film friction (without any treatment) for various lubricants.

The dynamic friction coefficients of thin films of IDL4, Zdol 2000 and A20H were measured on the surfaces of magnetic hard disks using a VINA™ contact start stop (CSS) tester which is attached to an OSA 5100™ optical surface analyzer (skew angle was −1.36°, vertical load was 2.5 g). As illustrated in FIG. 4, the results showed that lubricant IDL4 has comparable dynamic friction coefficients to those of the tested conventional lubricants.

Example 7

Thermal Stability Test

TGA experiments were conducted to observe the relative thermal stability in air. The temperatures of weight loss at 5% are given in Table 4.

TABLE 4

Decomposition Temperature Comparison

| lubricant | Temp. at weight loss @ 5% (° C.) |
|---|---|
| IDL4 | 260 |
| Z-DOL(2K) | 183 |
| Z-DOL(4K) | 200 |
| X1-p | 304 |
| A20H(3K) | 319[a] |
| Z-tetraol | 230[a] |

[a]Reference data

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A compound of formula (I)

wherein n in formula (I) is 0, 1, 2, 3, or 4;

m in formula (I) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F;

each OAr$_f$ is a different or a same fluorinated C6-C20 aryloxy group; and

R$_f$ is selected from the group consisting of CF$_2$CF$_2$O(CF$_2$CF$_2$O)$_r$CF$_2$CF$_2$ wherein r is 2 to 30 and CF$_2$(OCF$_2$CF$_2$)$_s$O(CF$_2$)$_t$ wherein s is 2 to 30 and t is 0, 1, 2, or 3.

2. The compound of claim 1, wherein n is 1, 2, 3, or 4.

3. The compound of claim 1 or 2, wherein each R', when present, is F.

4. The compound of claim 1, wherein m is 0.

5. The compound of claim 1, wherein OAr$_f$ is selected from the group consisting of 4-(trifluoromethyl)phenoxy, 4-fluorophenoxy, and pentafluorophenoxy.

6. The compound of claim 1, wherein R$_f$ is CF$_2$CF$_2$O(CF$_2$CF$_2$CF$_2$O)$_r$CF$_2$CF$_2$ where r is 21.

7. The compound of claim 1, wherein R$_f$ is CF$_2$(OCF$_2$CF$_2$)$_s$O(CF$_2$)$_t$ where s is 2 and t is 3.

8.

9. An intermediate compound of formula (IIa) or (IIb)

wherein n in formula (IIa) or (IIb) is 4 or 5;

m in formula (IIa) or (IIb) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F.

10. A method for forming the intermediate compound of formula (IIa) or (IIb)

-continued wherein n in formula (IIa) or (IIb) is 4 or 5;

m in formula (IIa) or (IIb) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F, the method comprising:

reacting hexachlorocyclotriphosphazene with a phenoxide of formula (IIIa) or (IIIb)

in a tetrahydrofuran solvent to form the intermediate compound of formula (IIa) or (IIb), respectively.

11. A method for forming the compound of formula (I)

wherein n in formula (I) is 0, 1, 2, 3, or 4;

m in formula (I) is 0, 1, 2, 3, or 4;

each R', when present, is a different or a same substituent selected from the group consisting of C1-C10 alkyl, C1-C10 alkoxy, C1-C10 perfluorinated alkyl, C1-C10 perfluorinated alkoxy, and F;

each OAr$_f$ is a different or a same fluorinated C6-C20 aryloxy group; and

$R_f$ is selected from the group consisting of $CF_2CF_2O(CF_2CF_2CF_2O)_rCF_2CF_2$ wherein r is 2 to 30 and $CF_2(OCF_2CF_2)_sO(CF_2)_t$ wherein s is 2 to 30 and t is 0, 1, 2, or 3, the method comprising:

reacting the intermediate compound of formula (IIa) or (IIb) with $NaOAr_f$ and $NaOCH_2$—$R_f$—$CF_3$ in a tetrahydrofuran solvent, wherein (IIa)

(IIb)

n in formula (IIa) or (IIb) is 4 or 5;
m in formula (IIa) or (IIb) is 0, 1, 2, 3, or 4;
each R', when present, is a different or a same substituent selected from the group consisting of C1-C10 alkyl, C1-C10 alkoxy, C1-C10 perfluorinated alkyl, C1-C10 perfluorinated alkoxy, and F;

$OAr_f$ in $NaOAr_f$ is a fluorinated C6-C20 aryloxy group; and $R_f$ is defined above.

12. A method for lubricating a magnetic recording medium, comprising applying a lubricant comprising a compound of formula (I)

(I)

wherein n in formula (I) is 0, 1, 2, 3, or 4;
m in formula (I) is 0, 1, 2, 3, or 4;
each R', when present, is a different or a same substituent selected from the group consisting of C1-C10 alkyl, C1-C10 alkoxy, C1-C10 perfluorinated alkyl, C1-C10 perfluorinated alkoxy, and F;
each $OAr_f$ is a different or a same fluorinated C6-C20 aryloxy group; and
$R_f$ is selected from the group consisting of $CF_2CF_2O(CF_2CF_2CF_2O)_rCF_2CF_2$ wherein r is 2 to 30 and $CF_2(OCF_2CF_2)_sO(CF_2)_t$ wherein s is 2 to 30 and t is 0, 1, 2, or 3.

* * * * *